United States Patent
Xu et al.

(10) Patent No.: US 8,884,075 B2
(45) Date of Patent: Nov. 11, 2014

(54) PROCESS FOR PRODUCING PHENOL

(75) Inventors: Teng Xu, Houston, TX (US); George Harry Gamble, Long Valley, NJ (US); Jihad Mohammed Dakka, Whitehouse Station, NJ (US); Lorenzo Cophard DeCaul, Langhorne, PA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 13/822,033

(22) PCT Filed: Aug. 25, 2011

(86) PCT No.: PCT/US2011/049130
§ 371 (c)(1),
(2), (4) Date: May 14, 2013

(87) PCT Pub. No.: WO2012/050665
PCT Pub. Date: Apr. 19, 2012

(65) Prior Publication Data
US 2014/0148620 A1 May 29, 2014

Related U.S. Application Data

(60) Provisional application No. 61/391,832, filed on Oct. 11, 2010.

(51) Int. Cl.
| | | |
|---|---|---|
| *C07C 37/07* | (2006.01) | |
| *B01J 35/02* | (2006.01) | |
| *C07C 2/74* | (2006.01) | |
| *B01J 23/40* | (2006.01) | |
| *C07C 407/00* | (2006.01) | |
| *C07C 45/53* | (2006.01) | |
| *C07C 37/08* | (2006.01) | |
| *B01J 37/02* | (2006.01) | |
| *B01J 23/38* | (2006.01) | |
| *B01J 23/58* | (2006.01) | |

(52) U.S. Cl.
CPC .............. *C07C 37/07* (2013.01); *B01J 35/023* (2013.01); *C07C 2/74* (2013.01); *B01J 23/40* (2013.01); *C07C 407/00* (2013.01); *C07C 45/53* (2013.01); *C07C 37/08* (2013.01); *C07C 2101/14* (2013.01); *B01J 37/0201* (2013.01); *B01J 23/38* (2013.01); *B01J 23/58* (2013.01)
USPC ........................................................ 568/799

(58) Field of Classification Search
USPC ........................................................ 568/799
See application file for complete search history.

(56) References Cited

U.S. PATENT DOCUMENTS

| | | | |
|---|---|---|---|
| 3,194,843 A | 7/1965 | Silber et al. | |
| 3,211,668 A | 10/1965 | Yamamoto | |
| 3,238,120 A | 3/1966 | Sale | |
| 3,358,044 A | 12/1967 | Russell et al. | |
| 3,514,492 A | 5/1970 | Juguin et al. | |
| 3,519,575 A | 7/1970 | Bozik et al. | |
| 3,534,110 A | 10/1970 | Juguin et al. | |
| 3,534,116 A | 10/1970 | Fuller | |
| 3,580,970 A | 5/1971 | Swift | |
| 3,691,102 A | 9/1972 | Swift | |
| 4,088,603 A | 5/1978 | Carter et al. | |
| 4,169,857 A | 10/1979 | Murtha | |
| 4,415,477 A * | 11/1983 | Rozovsky et al. | ............ 502/178 |
| 4,417,076 A | 11/1983 | Rozovsky et al. | |
| 4,929,762 A | 5/1990 | Matsunaga et al. | |
| 4,933,507 A | 6/1990 | Inoki et al. | |
| 4,999,326 A | 3/1991 | Sikkenga et al. | |
| 5,087,792 A | 2/1992 | Cottrell et al. | |
| 5,256,348 A | 10/1993 | Waller | |
| 5,310,713 A | 5/1994 | Kojima et al. | |
| 5,395,976 A | 3/1995 | Scharschmidt et al. | |
| 6,037,513 A | 3/2000 | Chang et al. | |
| 6,579,821 B1 | 6/2003 | Ginosar et al. | |
| 6,916,756 B2 | 7/2005 | Schindler et al. | |
| 7,256,149 B2 | 8/2007 | Grey et al. | |
| 7,285,685 B2 | 10/2007 | Walsdorff et al. | |
| 2011/0037022 A1 | 2/2011 | Dakka et al. | |

FOREIGN PATENT DOCUMENTS

| | | |
|---|---|---|
| GB | 640363 | 7/1950 |
| GB | 1362284 | 8/1974 |

OTHER PUBLICATIONS

Arends et al., "*Selective Catalytic Oxidation of Cyclohexylbenzene to Cyclohexylbenzene-1-Hydroperoxide: A Coproduct-Free Route to Phenol*", Tetrahedron, vol. 58, pp. 9055-9061 (2002).

* cited by examiner

*Primary Examiner* — Brian J Davis
(74) *Attorney, Agent, or Firm* — Jamie L. Sullivan; Siwen Chen (57) ABSTRACT

In a process for the dehydrogenation of cyclohexanone to produce phenol, cyclohexanone is contacted in a reaction zone under dehydrogenation conditions with a dehydrogenation catalyst comprising (i) a support comprising silica; and (ii) a dehydrogenation component comprising at least one metal selected from Group 10 of Periodic Table of Elements. Contact of the dehydrogenation catalyst with the cyclohexanone is then terminated and the dehydrogenation catalyst is contacted with an inert gas and/or hydrogen at a temperature of at least 300° C. Contact of the dehydrogenation catalyst with additional cyclohexanone is subsequently reestablished.

17 Claims, 3 Drawing Sheets

PROCESS FOR PRODUCING PHENOL

PRIORITY CLAIM TO RELATED APPLICATIONS

This application is a National Stage Application of International Application No. PCT/US2011/049130 filed Aug. 25, 2011, which claims priority to and the benefit of U.S. Provisional Application Ser. No. 61/391,832 filed Oct. 11, 2010, the disclosure of which is fully incorporated herein by reference.

FIELD

The present invention relates to a process for producing phenol.

BACKGROUND

Phenol is an important product in the chemical industry and is useful in, for example, the production of phenolic resins, bisphenol A, $\epsilon$-caprolactam, adipic acid, and plasticizers.

Currently, the most common route for the production of phenol is the Hock process via cumene. This is a three-step process in which the first step involves alkylation of benzene with propylene to produce cumene, followed by oxidation of the cumene to the corresponding hydroperoxide and then cleavage of the hydroperoxide to produce equimolar amounts of phenol and acetone. However, the world demand for phenol is growing more rapidly than that for acetone. In addition, due to a developing shortage, the cost of propylene is likely to increase. Thus, a process that uses higher alkenes instead of propylene and coproduces higher ketones, rather than acetone, may be an attractive alternative route to the production of phenols.

One such process involves the hydroalkylation of benzene to produce cyclohexylbenzene, followed by the oxidation of the cyclohexylbenzene (analogous to cumene oxidation) to cyclohexylbenzene hydroperoxide, which is then cleaved to produce phenol and cyclohexanone in substantially equimolar amounts. Such a process is described in, for example, U.S. Pat. No. 6,037,513.

However, although cyclohexanone is a valuable product with a growing market, there is currently no large worldwide merchant market for cyclohexanone and so most cyclohexanone is made as an intermediate and consumed on the spot. To obviate this problem it has been proposed to integrate the cyclohexylbenzene oxidation process with a dehydrogenation step whereby at least part of the cyclohexanone is converted to additional phenol (see co-pending International Patent Application Serial No. PCT/US2009/037223). To date, however, only limited research has been conducted into optimizing the process of dehydrogenating cyclohexanone to phenol.

For example, U.S. Pat. No. 3,534,110 discloses a process for the catalytic dehydrogenation of cyclohexanone and/or cyclohexanol to phenol over a catalyst comprising platinum and preferably iridium on a silica support, which also contains 0.5 to 3 wt % of an alkali or alkaline earth metal compound.

U.S. Pat. No. 4,933,507 discloses that phenol can be produced by dehydrogenating cyclohexenone through a vapor-phase reaction in the presence hydrogen using a solid-phase catalyst having platinum and alkali metal carried on a support. The catalyst support proposed in the '507 patent is silica, silica-alumina or alumina.

U.S. Pat. No. 7,285,685 discloses a process for the dehydrogenation of a saturated carbonyl compound, such as cyclohexanone, in the gas phase over a heterogeneous dehydrogenation catalyst comprising platinum and/or palladium and tin on an oxidic support, such as zirconium dioxide and/or silicon dioxide. In addition, the dehydrogenation catalyst can further comprise one or more elements of Groups I and/or II, preferably potassium and/or cesium, which are added to the catalyst as aqueous solutions of compounds which can be converted into the corresponding oxides by calcination.

One problem that has been encountered in the use of supported noble metal catalysts in the dehydrogenation of cyclohexanone is that the activity of the noble metal decreases fairly rapidly with time on stream, especially at economically attractive space velocities. There is therefore a need for a simple, cost effective and non-destructive process for periodically recovering the catalyst activity. However, although air calcination is frequently used to reactivate noble metal-containing catalysts, it has been found that using air calcination tends to be accompanied by migration and agglomeration of the noble metal on the support thereby resulting in reduction in metal surface area and therefore a reduction in catalyst activity.

According to the present invention, it has now been found that contacting the catalyst with hydrogen at a temperature of at least 300° C. is effective in restoring the activity of a supported noble metal catalyst used in the dehydrogenation of cyclohexanone. In addition, an analogous process, high temperature contact of the catalyst with a non-oxidizing atmosphere, such as hydrogen or nitrogen, can be used to protect the catalyst during temporary idling of the cyclohexanone dehydrogenation reactor required, for example, to allow maintenance on the dehydrogenation product separation train.

SUMMARY

In one aspect, the invention resides in a process for the dehydrogenation of cyclohexanone to produce phenol, the process comprising:

(a) contacting cyclohexanone in a reaction zone under dehydrogenation conditions with a dehydrogenation catalyst comprising (i) a support comprising silica; and (ii) a dehydrogenation component comprising at least one metal selected from Group 10 of the Periodic Table of Elements;

(b) terminating contact of the dehydrogenation catalyst with the cyclohexanone; then (c) supplying at least one interim gas to the reaction zone wherein the interim gas is selected from an inert gas or hydrogen gas and wherein the interim gas contacts the dehydrogenation catalyst at temperatures above about 300 C; and then (d) recontacting the dehydrogenation catalyst with additional cyclohexanone.

In another aspect, the invention resides in a process for the dehydrogenation of cyclohexanone to produce phenol, the process consisting of:

(a) contacting cyclohexanone in a reaction zone under dehydrogenation conditions with a dehydrogenation catalyst comprising (i) a support comprising silica; and (ii) a dehydrogenation component comprising at least one metal selected from Group 10 of the Periodic Table of Elements;

(b) terminating contact of the dehydrogenation catalyst with the cyclohexanone; then (c) contacting the dehydrogenation catalyst with hydrogen at a temperature of at least 300° C.; and then (d) recontacting the dehydrogenation catalyst with the cyclohexanone.

Conveniently, the contacting (c) is conducted at a pressure of from 100 to 1480 kPa for a time of at least 0.5 hours.

Conveniently, the contacting step (c) occurs in the substantial absence of oxygen.

In one embodiment, the contacting (c) is with hydrogen and causes at least partial reactivation of the dehydrogenation catalyst.

In another embodiment, the contacting step (c) causes the activity of the dehydrogenation catalyst to be substantially maintained.

Conveniently, the dehydrogenation catalyst further comprises at least 0.1 wt % of a metal promoter comprising at least one metal component selected from Group 1 and 2 of the Periodic Table of Elements.

In one embodiment, the dehydrogenation catalyst has an oxygen chemisorption of greater than 50%.

Conveniently, the dehydrogenation component comprises palladium and/or platinum.

Conveniently, the dehydrogenation conditions include a temperature of about 250° C. to about 500° C., a pressure of about 100 to about 3550 kPa, a weight hourly space velocity of about 0.2 to 50 $hr^{-1}$, and a hydrogen to cyclohexanone molar ratio of about 2 to about 20.

DETAILED DESCRIPTION OF THE EMBODIMENTS

Described herein is a process for producing phenol by the dehydrogenation of cyclohexanone. More particularly, there is described an integrated process for producing phenol from benzene, in which the benzene is converted to cyclohexylbenzene, which is then oxidized and cleaved to produce phenol and cyclohexanone, and the cyclohexanone in the resultant product is then deydrogenated to generate additional phenol.

Production of Cyclohexylbenzene

The first step in the present integrated process for producing phenol comprises conversion of benzene to cyclohexylbenzene. This can be achieved by any known technique, including direct alkylation of benzene with cyclohexene in the presence of an acid catalyst, such as zeolite beta or an MCM-22 family molecular sieve, or by oxidative coupling of benzene to biphenyl followed by hydrogenation of the biphenyl. However, in practice, the cyclohexylbenzene is generally produced by contacting benzene with hydrogen under hydroalkylation conditions in the presence of a hydroalkylation catalyst whereby the benzene undergoes the following reaction (1) to produce cyclohexylbenzene (CHB):

Any commercially available benzene feed can be used in the hydroalkylation step, but preferably the benzene has a purity level of at least 99 wt %. Similarly, although the source of hydrogen is not critical, it is generally desirable that the hydrogen is at least 99 wt % pure.

Conveniently, the total feed to the hydroalkylation step contains less than 1000 ppm, such as less than 500 ppm, for example less than 100 ppm, water. In addition, the total feed typically contains less than 100 ppm, such as less than 30 ppm, for example less than 3 ppm, sulfur and less than 10 ppm, such as less than 1 ppm, for example less than 0.1 ppm, nitrogen.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between about 100° C. and about 400° C., such as between about 125° C. and about 250° C., while suitable reaction pressures are between about 100 and about 7,000 kPa, such as between about 500 and about 5,000 kPa. Suitable values for the molar ratio of hydrogen to benzene are between about 0.15:1 and about 15:1, such as between about 0.4:1 and about 4:1 for example between about 0.4 and about 0.9:1.

The catalyst employed in the hydroalkylation reaction is a bifunctional catalyst comprising a molecular sieve of the MCM-22 family and a hydrogenation metal. The term "MCM-22 family material" (or "material of the MCM-22 family" or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference;)

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material (b) are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325); PSH-3 (described in U.S. Pat. No. 4,439,409); SSZ-25 (described in U.S. Pat. No. 4,826,667); ERB-1 (described in European Patent No. 0293032); ITQ-1 (described in U.S. Pat. No. 6,077,498); ITQ-2 (described in International Patent Publication No. WO97/17290); MCM-36 (described in U.S. Pat. No. 5,250,277); MCM-49 (described in U.S. Pat. No. 5,236,575); MCM-56 (described in U.S. Pat. No. 5,362,697); UZM-8 (described in U.S. Pat. No. 6,756,030); and mixtures thereof. Preferably, the molecular sieve is selected from (a) MCM-49, (b) MCM-56 and (c) isotypes of MCM-49 and MCM-56, such as ITQ-2.

Any known hydrogenation metal can be employed in the hydroalkylation catalyst, although suitable metals include palladium, ruthenium, nickel, zinc, tin, and cobalt, with palladium being particularly advantageous. Generally, the amount of hydrogenation metal present in the catalyst is between about 0.05 and about 10 wt %, such as between about 0.1 and about 5 wt %, of the catalyst. In one embodiment, where the MCM-22 family molecular sieve is an aluminosilicate, the amount of hydrogenation metal present is such that the molar ratio of the aluminum in the molecular sieve to the hydrogenation metal is from about 1.5 to about 1500, for example from about 75 to about 750, such as from about 100 to about 300.

An inorganic oxide may be employed in such a composite hydroalkylation catalyst provided it is stable and inert under the conditions of the hydroalkylation reaction. Suitable inorganic oxides include oxides of Groups 2, 4, 13 and 14 of the Periodic Table of Elements, such as alumina, titania, and/or zirconia. As used herein, the numbering scheme for the Periodic Table Groups is as disclosed in Chemical and Engineering News, 63(5), 27 (1985).

Suitable binder materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

Although the hydroalkylation step is highly selective towards cyclohexylbenzene, the effluent from the hydroalkylation reaction will normally contain some dialkylated products, as well as unreacted aromatic feed and the desired monoalkylated species. The unreacted aromatic feed is normally recovered by distillation and recycled to the alkylation reactor. The bottoms from the benzene distillation are further distilled to separate the monocyclohexylbenzene product from any dicyclohexylbenzene and other heavies. Depending on the amount of dicyclohexylbenzene present in the reaction effluent, it may be desirable to either (a) transalkylate the dicyclohexylbenzene with additional benzene or (b) dealkylate the dicyclohexylbenzene to maximize the production of the desired monoalkylated species.

Transalkylation with additional benzene is typically effected in a transalkylation reactor, separate from the hydroalkylation reactor, over a suitable transalkylation catalyst, such as a molecular sieve of the MCM-22 family, zeolite beta, MCM-68 (see U.S. Pat. No. 6,014,018), zeolite Y and mordenite. The transalkylation reaction is typically conducted under at least partial liquid phase conditions, which suitably include a temperature of about 100 to about 300° C., a pressure of about 800 to about 3500 kPa, a weight hourly space velocity of about 1 to about 10 $hr^{-1}$ on total feed, and a benzene/dicyclohexylbenzene weight ratio about of 1:1 to about 5:1.

The cyclohexylbenzene product from the hydroalkylation reaction and any downstream transalkylation or dealkylation reaction is separated from the reaction effluent(s) and is fed to the oxidation reaction described in more detail below.

Cyclohexylbenzene Oxidation

In order to convert the cyclohexylbenzene into phenol and cyclohexanone, the cyclohexylbenzene is initially oxidized to the corresponding hydroperoxide. This is accomplished by introducing an oxygen-containing gas, such as air, into a liquid phase containing the cyclohexylbenzene. Unlike cumene, atmospheric air oxidation of cyclohexylbenzene in the absence of a catalyst is very slow and hence the oxidation is normally conducted in the presence of a catalyst.

Suitable catalysts for the cyclohexylbenzene oxidation step are the N-hydroxy substituted cyclic imides described in U.S. Pat. No. 6,720,462 and incorporated herein by reference, such as N-hydroxyphthalimide, 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt or N-hydroxy-o-benzenedisulphonimide. Preferably, the catalyst is N-hydroxyphthalimide. Another suitable catalyst is N,N',N''-thihydroxyisocyanuric acid.

These materials can be used either alone or in the presence of a free radical initiator and can be used as liquid-phase, homogeneous catalysts or can be supported on a solid carrier to provide a heterogeneous catalyst. Typically, the N-hydroxy substituted cyclic imide or the N,N',N''-trihydroxyisocyanuric acid is employed in an amount between 0.0001 mol % to 15 wt %, such as between 0.001 mol % to 5 wt %, of the cyclohexylbenzene.

Suitable conditions for the oxidation step include a temperature between about 70° C. and about 200° C., such as about 90° C. to about 130° C., and a pressure of about 50 to 10,000 kPa. Any oxygen-containing gas, preferably air, can be used as the oxidizing medium. The reaction can take place in batch reactors or continuous flow reactors. A basic buffering agent may be added to react with acidic by-products that may form during the oxidation. In addition, an aqueous phase may be introduced, which can help dissolve basic compounds, such as sodium carbonate.

Hydroperoxide Cleavage

The final reactive step in the conversion of the cyclohexylbenzene into phenol and cyclohexanone involves cleavage of the cyclohexylbenzene hydroperoxide, which is conveniently effected by contacting the hydroperoxide with a catalyst in the liquid phase at a temperature of about 20° C. to about 150° C., such as about 40° C. to about 120° C., a pressure of about 50 to about 2,500 kPa, such as about 100 to about 1000 kPa. The cyclohexylbenzene hydroperoxide is preferably diluted in an organic solvent inert to the cleavage reaction, such as methyl ethyl ketone, cyclohexanone, phenol or cyclohexylbenzene, to assist in heat removal. The cleavage reaction is conveniently conducted in a catalytic distillation unit.

The catalyst employed in the cleavage step can be a homogeneous catalyst or a heterogeneous catalyst.

Suitable homogeneous cleavage catalysts include sulfuric acid, perchloric acid, phosphoric acid, hydrochloric acid and p-toluenesulfonic acid. Ferric chloride, boron trifluoride, sulfur dioxide and sulfur trioxide are also effective homogeneous cleavage catalysts. The preferred homogeneous cleavage catalyst is sulfuric acid, with preferred concentrations in the range of 0.05 to 0.5 wt %. For a homogeneous acid catalyst, a neutralization step preferably follows the cleavage step. Such a neutralization step typically involves contact with a basic component, with subsequent decanting of a salt-enriched aqueous phase.

A suitable heterogeneous catalyst for use in the cleavage of cyclohexylbenzene hydroperoxide includes a smectite clay, such as an acidic montmorillonite silica-alumina clay, as described in U.S. Pat. No. 4,870,217, the entire disclosure of which is incorporated herein by reference.

Dehydrogenation of the Cyclohexanone

The effluent from the cleavage reaction comprises phenol and cyclohexanone in substantially equimolar amounts. The present process provides an advantageous route for increasing the amount of phenol produced from the original benzene feed by contacting at least part of the cleavage effluent with a dehydrogenation catalyst so as to convert some or all of the cyclohexanone in the effluent into additional phenol according to the reaction (2):

(2)

Cyclohexanone and phenol produce an azeotropic mixture composed of 28 wt % cyclohexanone and 72 wt % phenol, so that any attempt to separate the effluent from the cyclohexylbenzene hydroperoxide cleavage step by simple distillation results in this azeotropic mixture. However, the efficiency of the separation can be enhanced by conducting the distillation under at least partial vacuum, typically at below 101 kPa. Moreover, extractive distillation processes are known for separating cyclohexanone and phenol, see for example, U.S. Pat. Nos. 4,021,490; 4,019,965; 4,115,207; 4,115,204; 4,115,206; 4,201,632; 4,230,638; 4,167,456; 4,115,205; and 4,016,049. Nevertheless, phenol/cyclohexanone separation remains a costly process, so that in one embodiment, the feed to the dehydrogenation step has the same composition as the cleavage effluent, thereby avoiding the need for an initial expensive separation step. Depending on the efficiency of the cyclohexanone dehydrogenation, the final product may contain substantially all phenol, thereby at least reducing the problem of separating the phenol from the cleavage effluent.

In another embodiment, the cleavage effluent is subjected to one or more separation processes to recover or remove one or more components of the effluent prior to dehydrogenation. In particular, the cleavage effluent is conveniently subjected to at least a first separation step to recover some or all of the phenol from the effluent, typically so that the effluent stream fed to the dehydrogenation reaction contains less than 50 wt %, for example less than 30 wt %, such as less than 1 wt %, phenol. The first separation step is conveniently effected by vacuum distillation and the same, or additional vacuum distillation steps, can be used to remove components boiling below 155° C. (as measured at 101 kPa); such as benzene and cyclohexene, and/or components boiling above 185° C. (as measured at 101 kPa); such as 2-phenyl phenol and diphenyl ether, prior to feeding the effluent stream to the dehydrogenation reaction.

The dehydrogenation catalyst used in reaction (2) comprises a support comprising silica, such as particulate silica, a silicate and/or an aluminosilicate, on which is deposited a hydrogenation-dehydrogenation component, typically comprising at least one metal or compound thereof selected from Group 10 of the Periodic Table of Elements. Generally, the hydrogenation-dehydrogenation component is selected from the noble metal platinum and palladium as well as compounds and mixtures thereof. Typically, the dehydrogenation catalyst contains between about 0.1 and about 10 wt % of the hydrogenation-dehydrogenation component.

In one embodiment, the catalyst further contains an inorganic base component, such as a potassium compound. Typically, the inorganic base component is present in an amount between about 0.1 and about 5 wt % of the catalyst.

The present dehydrogenation catalyst may be prepared by initially treating the support, normally by impregnation, with a liquid composition comprising the hydrogenation-dehydrogenation component or a precursor thereof, the optional inorganic base component and at least one organic dispersant selected from an amino alcohol and an amino acid. The organic dispersant may be dispersed in a liquid carrier. The liquid carrier is generally water. Examples of amino alcohols include wherein the amino alcohol is selected from the group consisting of methanolamine, dimethanolamine, tr-methanolamine, ethanolamine, di-ethanolamine, triethanolamine, butanolamine, dibutanolamine, tributanolamine, propanolamine, dipropanaolamine, tripropanolamine, N,N,-dialkyl-ethanolamines, N-alkyl-diethanolamines, N-alkyl-ethanolamines, N,N,-dialkyl-propanolamines, N-alkyl-dipropanolamines, N-alkyl-propanolamines, N,N,-dialkyl-propanolamines, N-alkyl-dipropanolamines, N-alkyl-propanolamines, N,N,-dialkyl-propanolamines, N-alkyl-dipropanolamines, N-alkyl-propanolamines, N,N,-dialkyl-butonolamines, N-alkyl-dibutanolamines, N-alkyl-butanolamines, N,N,-dialkyl-butanolamines, N-alkyl-dibutanolamines, N-alkyl-butanolamines, N,N,-dialkyl-hexanolamines, N-alkyl-dihexanolamines, N-alkyl-hexanolamines, N,N,-dialkyl-hexanolamines, N-alkyl-dihexanolamines, N,N,-dialkyl-heptanolamines, N-alkyl-diheptanolamines, N-alkyl-heptanolamines, N,N,-dialkyl-heptanolamines, N-alkyl-diheptanolamines, N-alkyl-heptanolamines. Examples of amino acids include alanine, arginine, asparagines, aspartic acid, cysteine, cystine, 3,5-dibromotyrosine, 3,5, diiodotyrosine, glutamic acid, glutamine, glycine, histidine, hydroxylysine, hydroxyproline, isoleucine, leucine, lysine, methionine, phenylalanine, proline, serine, threonine, thyroxine, tryptophane, tyrosine and valine, with arginine being preferred.

Generally, the organic dispersant is present in the liquid composition in an amount between about 1 and about 20 wt % of the composition. After treatment with the liquid composition, the support is dried to remove the liquid carrier and is then heated in an oxidizing atmosphere, generally in air, under conditions to decompose substantially all of the organic dispersant. Suitable conditions for removing the dispersant include a temperature of about 100° C. to about 600° C. for a time of about 0.5 to about 50 hours. The catalyst may then be heated in a reducing atmosphere, such as hydrogen, at a temperature of about 50° C. to about 500° C. for a time of about 0.5 to about 10 hours to reduce the hydrogenation-dehydrogenation component.

It is found that adding the organic dispersant to the liquid composition used to deposit the hydrogenation-dehydrogenation metal on the support results in more uniform and smaller crystal size metal particles on the support, which in turn produces a more deactivation-resistant catalyst. The improved metal dispersion can be measured by oxygen chemisorption, with the catalyst produced by the present method typically exhibiting an oxygen chemisorption value in excess of 50%.

As used herein, the oxygen chemisorption value of a particular catalyst is a measure of metal dispersion on the catalyst and is defined as the ratio of the number of moles of atomic oxygen sorbed by the catalyst to the number of moles of dehydrogenation metal contained by the catalyst. The oxygen chemisorption values referred to herein are measured using the following technique.

Chemisorption measurements are obtained under static high vacuum conditions on a Quantachrome Autosorb 1A instrument. Approximately 0.3-0.5 grams of catalyst are loaded into a quartz cell and dried in flowing He by heating at 4° C./min to 130° C. and holding for 1 hour. The flow is then switched to hydrogen and the catalyst is reduced in flowing hydrogen by heating at 2° C./min to 425° C., holding isothermal for 2 hours, and then cooling to 400° C. in flowing hydrogen. Following reduction, the sample is evacuated (while still at 400° C.) with a turbomolecular pump for 30 minutes to remove any chemisorbed hydrogen. With the sample still under vacuum, the temperature is lowered to 40° C. and held isothermal during subsequent experiments. An 8-point isotherm (with pressures between 80 and 400 torr) is measured at 40° C. with $O_2$ as the adsorbent molecule. Extrapolation of the linear portion of this curve to zero pressure gives the total or combined adsorption uptake.

Suitable conditions for the dehydrogenation step comprise a temperature of about 250° C. to about 500° C., a pressure of about 100 to about 3550 kPa, a weight hourly space velocity of about 0.2 to 50 $hr^{-1}$ and a hydrogen to cyclohexanone molar ratio of about 2 to about 20. Typical conditions include a temperature of about 300° C. to about 450° C., a pressure of about 1 atm to about 3 atm (100 kPa to 300 kPa) a WHSV of about 1 to about 15 $hr^{-1}$ and a hydrogen to cyclohexanone molar ratio of about 1:1 to about 4:1.

The reactor configuration used for the dehydrogenation process generally comprises one or more fixed bed reactors containing a solid catalyst with a dehydrogenation function. Initial per-pass conversion of cyclohexanone is greater than 70%, and typically greater than 90%. Provision can be made for the endothermic heat of reaction, preferably by multiple adiabatic beds with interstage heat exchangers. The temperature of the reaction stream drops across each catalyst bed, and then is raised by the heat exchangers. Preferably, 3 to 5 beds are used, with a temperature drop of 30 to 100° C. across each bed. Preferably the last bed in the series runs at a higher exit temperature than the first bed in the series.

Although the present dehydrogenation process is highly selective to production of phenol, it is found that the activity of the catalyst and hence the degree of conversion of the cyclohexanone falls significantly with time on stream, especially at economically attractive WHSV values. Thus the catalyst must undergo frequent reactivation. In the present process, this is achieved by terminating contact of the dehydrogenation catalyst with the cyclohexanone, typically when the activity of the catalyst has fallen below 90% of its initial value.

In one embodiment, after terminating the supply of cyclohexanone, the dehydrogenation catalyst is then contacted with an interim gas at a temperature of at least 300° C. and typically at about 350° C. to about 500° C. Conveniently, the majority of the interim gas contacting occurs at temperatures above about 300° C. based on contacting time. Conveniently, the contacting with the interim gas is conducted at a pressure of about 100 to about 1480 kPa for a time of at least 0.5 hours, for example from about 0.5 to about 10 hours, typically to return at least a portion of the activity of the catalyst to its initial value. After reactivation, contact between the dehydrogenation catalyst and the cyclohexanone feed can be reestablished and the cycle of dehydrogenation and reactivation can be repeated. Conveniently, the interim gas contacting may occur in the substantial absence of oxygen. The at least interim gas may be selected from hydrogen gas or an inert gas or both. The interim gas is chosen from a group consisting of hydrogen gas, at least one inert gas, or a combination thereof In one embodiment, after terminating the supply of cyclohexanone, the dehydrogenation catalyst is then contacted with hydrogen at a temperature of at least 300° C. and typically at about 300° C. to about 500° C. or at about 300° C. to about 400° C. Conveniently, the dehydrogenation catalyst may be contacted with hydrogen at a temperature of less than 400° C. Conveniently, the majority of the hydrogen contacting embodiment based on contacting time occurs at temperatures of less than 400° C. in one embodiment and above about 300° C. in other embodiments and between 300° C. and 400° C. in still another embodiment. Conveniently, the contacting with hydrogen is conducted at a pressure of about 100 to about 1480 kPa for a time of at least 0.5 hours, for example from about 0.5 to about 10 hrs, typically to return at least a portion of the activity of the catalyst to its initial value. After reactivation, contact between the dehydrogenation catalyst and the cyclohexanone feed can be reestablished and the cycle of dehydrogenation and reactivation can be repeated. Conveniently, the hydrogen contacting may occur in the substantial absence of oxygen.

In another embodiment, after terminating the supply of cyclohexanone, the dehydrogenation catalyst is then contacted with hydrogen at a temperature of at least 300° C. Conveniently, the majority of the hydrogen contacting occurs at temperatures above about 300° C. based on contacting time. Conveniently, the contacting with hydrogen is conducted at a pressure of about 100 to about 1480 kPa for a time of at least 0.5 hours, for example from about 0.5 to about 10 hr. Providing this contacting, it is found that the hydrogen treatment can be continued for a period of time with the activity of the catalyst being substantially maintained (i.e., the cyclohexanone conversion activity being decreased by less than 5%). Such hydrogen treatment can be useful in protecting the catalyst during temporary idling of the cyclohexanone dehydrogenation reactor required, for example, to allow maintenance on the dehydrogenation product separation train. Conveniently, the hydrogen contacting may occur in the substantial absence of oxygen. After the hydrogen contacting step, contact between the dehydrogenation catalyst and the cyclohexanone feed can be reestablished and the cycle of dehydrogenation and reactivation can be repeated.

In one embodiment, the hydrogen is supplied to the reactor in the form of hydrogen gas comprising at least 10 mol % hydrogen, at least 20 mol % hydrogen, at least 30 mol % hydrogen, at least 40 mol % hydrogen, at least 50 mol % hydrogen, at least 60 mol % hydrogen, at least 70 mol % hydrogen, at least 80 mol % hydrogen, at least 90 mol % hydrogen, at least 95 mol % hydrogen, and at least 99 mol % hydrogen.

In a further embodiment, the supply of cyclohexanone and hydrogen are temporarily suspended and the dehydrogenation catalyst is then contacted with an inert gas, such as nitrogen, helium and/or argon, at a temperature of at least 300° C. and typically at about 350° C. to about 500° C. Conveniently, the majority of the inert gas contacting occurs at temperatures above about 300° C. based on contacting time. Providing this contacting is conducted in the absence of oxygen, it is found that the inert gas treatment can be continued for a period of time with the activity of the catalyst being substantially maintained (i.e., the cyclohexanone conversion activity being decreased by less than 5%). Such inert gas treatment can be useful in protecting the catalyst during temporary idling of the cyclohexanone dehydrogenation reactor required, for example, to allow maintenance on the dehydrogenation product separation train.

In one embodiment, the inert gas is supplied to reactor and the inert gas comprises at least 10 mol % inert gas, at least 20 mol % inert gas, at least 30 mol % inert gas, at least 40 mol % inert gas, at least 50 mol % inert gas, at least 60 mol % inert gas, at least 70 mol % inert gas, at least 80 mol % inert gas, at least 90 mol % inert gas, at least 95 mol % inert gas, and at least 99 mol % inert gas.

In other embodiments, the supply of cyclohexanone and hydrogen are temporarily suspended and the dehydrogenation catalyst is then contacted with the interim gas, at a temperature of at least 250° C. In still other embodiments, the temperature lower limit for contacting with the interim gas may be 300° C., 310° C., 320° C., 330° C., 340° C., 350° C., 360° C., 370° C., 380° C., 390° C., 400° C., 410° C., 420° C., 430° C., 440° C., 450° C., 500° C., 550° C., and 600° C.; and the upper limit temperature may be 400° C., 410° C., 420° C., 430° C., 440° C., 450° C., 460° C., 470° C., 480° C., 490° C., 500° C., 510° C., 520° C., 530° C., 540° C., 550° C., 600° C., 650° C., 700° C., and 750° C. with ranges from any lower limit to any upper limit being contemplated. In still other embodiments, the majority of the interim gas contacting occurs at these temperature ranges based on contacting time.

The invention will now be more particularly described with reference to the following non-limiting Examples and the accompanying drawings.

Example 1

Preparation of 0.8 wt % Pt/1 wt % K/SiO2 Catalyst 0.403 g hexachloroplatinic acid was dissolved in 25 cc (4:1 wt ratio) acetone/water mixture and to this solution were added 20 g SiO2 extrudates (surface area 130 m2/g, 300-400 Å pore diameter). The resultant mixture was left overnight at room temperature for solvent evaporation, then dried at 100° C. 0.71 g of potassium carbonate was dissolved in 25 cc (4:1 wt ratio) acetone/water mixture and the resultant solution was added to the Pt/SiO2 extrudates sample. The mixture was left overnight at room temperature for solvent evaporation, then dried at 100° C. to produce a 0.8 wt % Pt/1 wt % K/SiO2 catalyst.

Example 2

Cyclohexanone Dehydrogenation and Hydrogen Rejuvenation

The reactor used in these experiments was a stainless steel tubular reactor having a length of 22 inch (56 cm), an external diameter of 0.5 inch (1.3 cm) and a wall thickness of 0.035 inch (0.09 cm). Two pieces of stainless steel tubing, one 0.375 inch (0.95 cm) in external diameter and the other 0.25 inch (0.64 cm) in external diameter and both 8.75 inch (22 cm) in length were mounted one inside of the other and used as a spacer in the bottom of the reactor to position and support the catalyst. A 0.25 inch (0.64 cm) plug of glass wool was placed at the top of the spacer to keep the catalyst in place.

The catalyst produced in Example 1 was pressed into pellets then crushed and sized to 20-40 US sieve mesh. 5.0 g of the pre-sized catalyst was then loaded into the reactor from the top to produce a catalyst bed of about 15 cm in length. A 0.125 inch (0.3 cm) diameter stainless steel thermo-well was placed in the catalyst bed to accommodate temperature scanning throughout the catalyst bed. A 0.125 inch (0.3 cm) plug of glass wool was placed at the top of the catalyst bed and the remaining void space at the top of the reactor was filled with quartz chips. The reactor was installed in a furnace with the catalyst bed in the middle of the furnace at a pre-marked isothermal zone. The reactor was then pressure and leak tested at 300 psig (2170 kPa).

The catalyst was pre-conditioned in situ by heating to the reaction temperature of 375° C. or 430° C. with $H_2$ flow at 100 cc/min and holding for 2 hours. After pre-conditioning, a 500 cc ISCO syringe pump was used to introduce cyclohexanone to the reactor. The feed was pumped through a vaporizer then through heated lines to the reactor, with separate experiments being conducted at cyclohexanone WHSV values of 1 and 2 $hr^{-1}$. A Brooks mass flow controller was used for hydrogen feed measurements. A Grove "Mity Mite" back pressure controller was used to control the reactor pressure. GC analyses were taken to verify feed composition. Dehydrogenation reactions were conducted at atmospheric pressure and 50 psig (446 kPa) and catalyst bed temperatures of 375° C. and 430° C.

The products exiting the reactor were routed through heated lines to two collection pots in series, while overhead gas products were routed to an on-line Hewlett Packard (HP) 5890 gas chromatograph. The first pot was heated to 60° C. and the second pot was cooled with chilled coolant to about 10° C. The product was collected for material balances over 12 hrs to 24 hrs intervals. Samples were taken and diluted with 50% ethanol for analysis. An HP 6890 gas chromatograph with a flame ionization detector (FID) and with an Agilent Technologies column 30 m×0.32 mm×0.25 micron film thickness was used for the analysis of the hydrocarbon products. Overhead gas products analyses were taken on line via the HP 5980 gas chromatograph with GW Scientific column 60 m×0.25 mm ID×1.0 micron film. The HP 6890GC analysis ramp program was set to: 40° C. for 0 min; 5° C./min to 150° C., held 0 min; 10° C./min to 260° C. and held 28 min for a total analysis time of 60 min. The HP 5890 GC ramp was set to: −30° C. for 5 min, 5° C./min to 80° C. for 2 min, 5° C./min to 200° C. for 0 min, 15° C./min to 240° C. and held to the total analysis time of 60 min.

Figure 1:
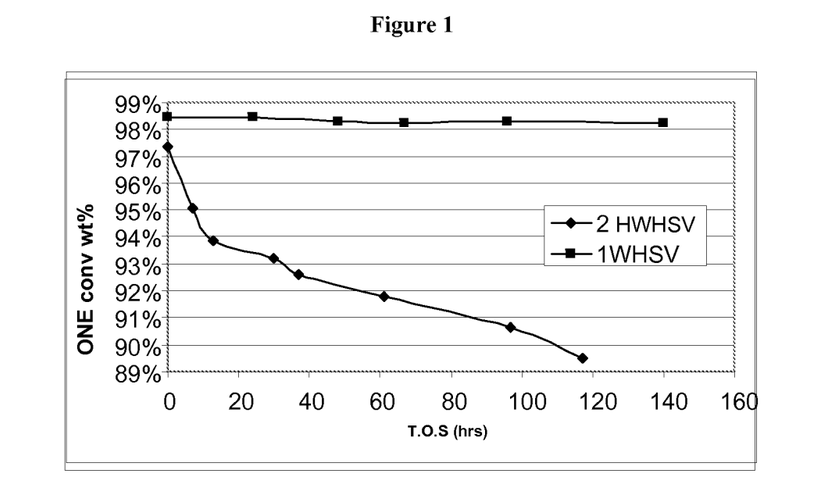
FIG. 1 is a graph of cyclohexanone conversion against time on stream at 375° C. and atmospheric pressure using WHSV values of 1 $hr^{-1}$ and 2 $hr^{-1}$ in the cyclohexanone dehydrogenation process of Example 2.
Figure 2:
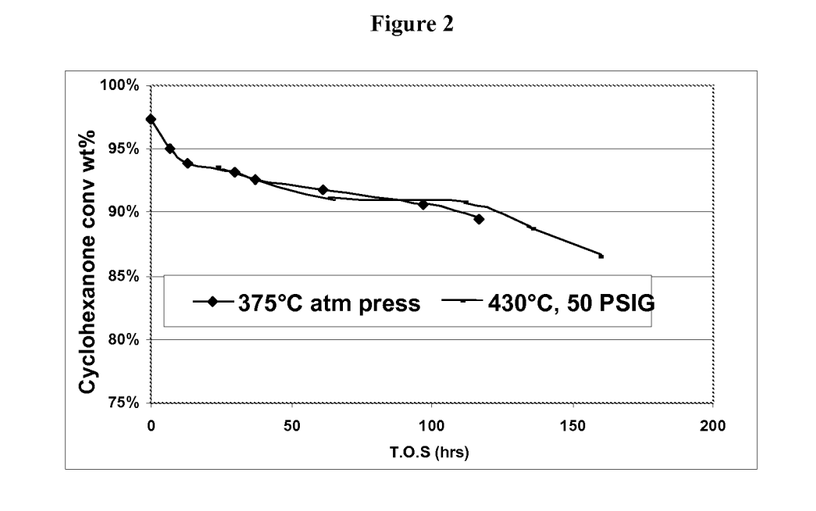
FIG. 2 is a graph of cyclohexanone conversion against time on stream at 375° C. and atmospheric pressure and at 430° C. and 50 psig (395 kPa) both using a WHSV value of 2 $hr^{-1}$ in the cyclohexanone dehydrogenation process of Example 2.

The results are summarized in FIGS. 1 and 2. In particular, FIG. 1 shows that when the dehydrogenation reaction was run at atmospheric pressure, a temperature of 375° C. and a WHSV of 1 hr$^{-1}$ the catalyst showed stability for more than 140 hours on stream. However, when the space velocity was increased to 2 hr$^{-1}$ to improve productivity, without change in the temperature or pressure, the catalyst exhibited rapid deactivation. As shown in FIG. 2, the catalyst showed similar rapid deactivation when the dehydrogenation reaction was run at 50 psig (446 kPa), a temperature of 430° C. and a WHSV of 2 hr$^{-1}$.

Figure 3:
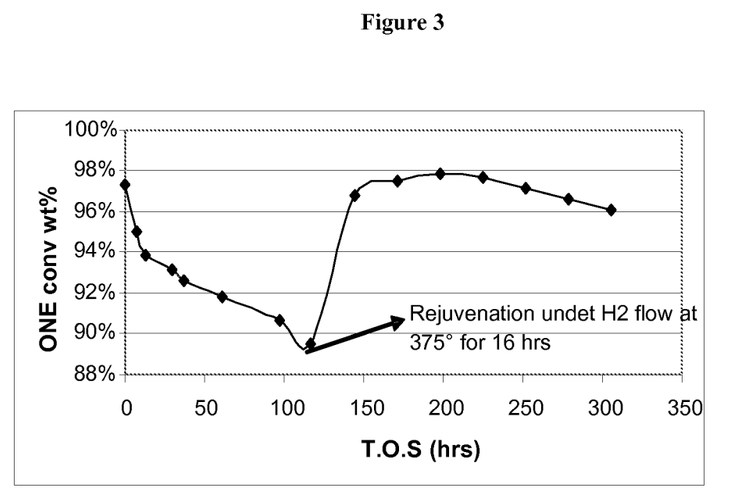
FIG. 3 is a graph of cyclohexanone conversion against time on stream at 375° C. and atmospheric pressure, both before and after hydrogen rejuvenation, in the cyclohexanone dehydrogenation process of Example 2.
Figure 4:
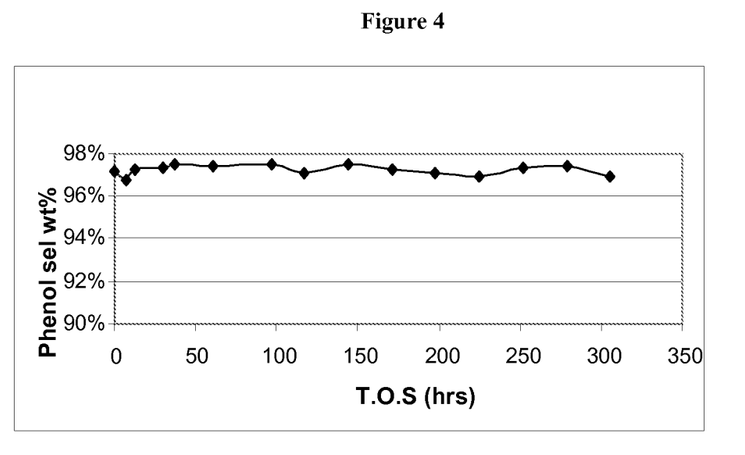
FIG. 4 is a graph of phenol selectivity against time on stream at 375° C. and atmospheric pressure, both before and after hydrogen rejuvenation, in the cyclohexanone dehydrogenation process of Example 2.
Figure 5:
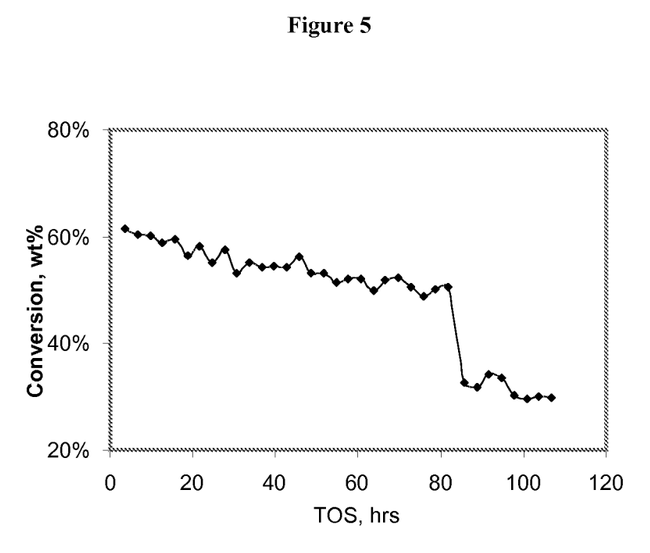
FIG. 5 is a graph of cyclohexanone conversion against time on stream at 375° C., 100 psig (790 kPa) and 15 WHSV in the cyclohexanone dehydrogenation process of Example 4.

FIGS. 3 and 4 show the effect of interrupting the cyclohexanone, but not the hydrogen, flow in the dehydrogenation reaction illustrated in FIG. 2 (atmospheric pressure, a temperature of 375° C. and a WHSV of 2 hr$^{-1}$) after 120 hours on stream and then treating the partially deactivated catalyst with hydrogen for 16 hours at atmospheric pressure and a temperature of 375° C. It will be seen from FIG. 3 that the hydrogen treatment returned the catalyst substantially to its original activity. In fact, after the cyclohexanone flow was reestablished, the rate of decrease of the cyclohexanone conversion with time on stream was significantly less than that exhibited by the fresh catalyst. As shown in FIG. 4, the phenol selectivity was substantially unaffected by the hydrogen rejuvenation and remained at almost 98% throughout the experiment.

Example 3

Preparation of 0.25 wt % Pt/1 wt % K/SiO2 Catalyst

A silica extrudate was impregnated using aqueous based incipient wetness impregnation with 0.25 wt % of Pt using tetraammine Pt nitrate solution. The sample was dried at 121° C. for 2 hrs followed by air calcination at 538° C. for 2 hrs. 1% K was impregnated onto the calcined sample containing 0.25 wt % Pt using a potassium carbonate solution. Following potassium impregnation, the sample was dried at 121° C. and then calcined in air at 538° C. for 2 hrs.

Example 4

Cyclohexanone Dehydrogenation and Air Treatment

The catalyst of Example 3 was used to convert cyclohexanone into phenol at 375° C., 100 psig (790 kPa), 15 WHSV and H$_2$/cyclohexanone molar ratio of 2.1. The result is shown in FIG. 1, which shows that the catalyst exhibited a cyclohexanone conversion of around 60 wt % at the start of the test but had deactivated to a cyclohexanone conversion of about 50 wt % after about 80 hours on stream.

To test the effect of air on catalyst activity, after about 80 hours on stream the cyclohexanone feed and hydrogen feed were stopped and air was allowed to flow through the catalyst bed at 450° C. for 2 hrs. After the air flow stopped, the catalyst bed temperature was lowered to 375° C. in hydrogen, and was maintained at 375° C. in hydrogen for 2 hrs to reduce Pt. Following hydrogen reduction, cyclohexanone and hydrogen feed were resumed to check for catalyst activity by measuring cyclohexanone conversion. The result is also shown in FIG. 1 and demonstrates there was a significant reduction in cyclohexanone conversion as a result of contact with air. In particular, cyclohexanone conversion decreased from 50% prior to air treatment to 32% after air treatment, a reduction of 36%.

The results clearly demonstrate that air contact with the supported Pt catalyst is detrimental to catalyst activity.

Example 5

Preparation of 1 wt % Pt/1 wt % K/SiO2 Catalyst 1 wt % K containing ½₀″ quadrulobe silica extrudate was prepared using potassium carbonate solution by aqueous based incipient wetness impregnation. After K impregnation, the sample was dried in air at 121° C. followed by calcination in air at 538° C. 1 wt % of Pt was then loaded onto 1% K/SiO2 by incipient wetness impregnation of tetraamine platinum nitrate. The sample was dried at 121° C. following platinum impregnation. The dried sample was then calcined at 350° C. in air.

Example 6

Cyclohexanone Dehydrogenation and Hydrogen Treatment

The catalyst of Example 5 was used to test the effect of hydrogen treatment on catalyst activity. The test was performed at 425° C., 100 psig (790 kPa), 15 WHSV and H$_2$/cyclohexanone molar ratio of 2.1. The conversion of cyclohexanone was measured to be 75.1% with a selectivity for phenol of 98.3 wt %. The catalyst was then treated in hydrogen flow at 425° C. for 44 hrs after the feed, i.e., cyclohexanone and hydrogen, was stopped. After the hydrogen treatment, cyclohexanone and hydrogen feed was resumed to check for catalyst activity and selectivity. The results are shown in Table 1 and demonstrate that the measured activity and selectivity were essentially identical to those prior to hydrogen treatment, suggesting that hydrogen would be a good choice for purging or maintaining activity for supported Pt catalysts.

TABLE 1

|  | Conversion, wt % | Phenol Selectivity, wt % |
| --- | --- | --- |
| Before H$_2$ Treatment | 75.1 | 98.3 |
| After H$_2$ Treatment | 74.7 | 98.3 |

Example 7

Cyclohexanone Dehydrogenation and Hydrogen Treatment

The catalyst of Example 5 was also used to test the effect of nitrogen treatment on catalyst activity. The test was performed at 425° C., 100 psig (790 kPa), 15 WHSV and H$_2$/cyclohexanone molar ratio of 2.1. The conversion of cyclohexanone was measured to be 74.7% with a selectivity for phenol of 98.3 wt %. The catalyst was then treated in nitrogen flow at 425° C. for 24 hrs after the feed, i.e., cyclohexanone and hydrogen, was stopped. After the nitrogen treatment, cyclohexanone and hydrogen feed was resumed to check for catalyst activity and selectivity. The results are shown in Table 1 and show that measured activity and selectivity were 68.8% and 98%, respectively. The treatment in nitrogen led to some reduction in activity from 74.7% to 68.8%, a reduction of 7.9%. The percent reduction is higher than that in hydrogen but significantly less than that in air. It seems to be acceptable to use nitrogen to maintain catalyst activity if hydrogen is not available. One advantage of using nitrogen instead of hydrogen is that nitrogen is cheaper.

TABLE 2

|  | Conversion, wt % | Phenol Selectivity, wt % |
|---|---|---|
| Before $N_2$ Treatment | 74.7 | 98.3 |
| After $N_2$ Treatment | 68.8 | 98.0 |

While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

The invention claimed is:

1. A process for the dehydrogenation of cyclohexanone to produce phenol, the process comprising:
   (a) contacting cyclohexanone in a reaction zone under dehydrogenation conditions with a dehydrogenation catalyst comprising (i) a support comprising silica; and (ii) a dehydrogenation component comprising at least one metal selected from Group 10 of the Periodic Table of Elements, wherein the dehydrogenation conditions include a temperature of about 250° C. to about 500° C., a pressure of about 100 to about 3550 kPa, a weight hourly space velocity of about 0.2 to 50 $hr^{-1}$, and a hydrogen to cyclohexanone molar ratio of about 2 to about 20;
   (b) terminating contact of the dehydrogenation catalyst with the cyclohexanone; then
   (c) supplying at least one interim gas to the reaction zone wherein the interim gas is selected from an inert gas or hydrogen gas and wherein the interim gas contacts the dehydrogenation catalyst at temperatures above about 300° C.; and then
   (d) recontacting the dehydrogenation catalyst with additional cyclohexanone.

2. The process of claim 1, wherein the contacting step (c) occurs for a period of at least one hour.

3. The process of claim 1, wherein the majority of the contacting step (c) occurs at temperatures between about 350° C. to about 500° C. based on contacting time.

4. The process of claim 1, wherein the majority of the contacting step (c) occurs at a temperature of less than 400° C. and at a pressure of less than 500 kPa and causes at least partial reactivation of the dehydrogenation catalyst.

5. The process of claim 1, wherein the contacting step (c) is conducted at a pressure of from 100 to 1480 kPa for a time of at least 0.5 hours.

6. The process of claim 1, wherein the interim gas is selected from helium gas, nitrogen gas, and argon gas.

7. The process of claim 1, wherein the at least one interim gas is hydrogen gas and wherein the interim gas comprises at least 10 mol % hydrogen.

8. The process of claim 1, wherein the at least one interim gas comprises at least 10 mol % inert gas.

9. The process of claim 1, wherein the process occurs in the absence of oxygen.

10. The process of claim 1, wherein the contacting step (c) is with hydrogen and causes at least partial reactivation of the dehydrogenation catalyst.

11. The process of claim 1, wherein the contacting step (c) causes the activity of the dehydrogenation catalyst to be maintained.

12. The process of claim 1, wherein the dehydrogenation catalyst further comprises at least 0.1 wt % of a metal promoter comprising at least one metal component selected from Group 1 and 2 of Periodic Table of Elements.

13. The process of claim 1, wherein the dehydrogenation catalyst has an oxygen chemisorption of greater than 50%.

14. The process of claim 1, wherein the dehydrogenation component comprises palladium and/or platinum.

15. The process of claim 1 and further comprising:
   (e) contacting benzene and hydrogen with a hydroalkylation catalyst under hydroalkylation conditions to convert at least part of the benzene to cyclohexylbenzene;
   (f) oxidizing at least part of the cyclohexylbenzene from contacting step (e) to produce cyclohexylbenzene hydroperoxide;
   (g) cleaving at least part of the cyclohexylbenzene hydroperoxide from oxidizing step (f) to produce phenol and cyclohexanone; and
   (h) feeding at least part of the cyclohexanone and at least part of the phenol from cleaving step (g) to the reaction zone.

16. A process for the dehydrogenation of cyclohexanone to produce phenol, the process comprising:
   (a) contacting cyclohexanone in a reaction zone under dehydrogenation conditions with a dehydrogenation catalyst comprising (i) a support comprising silica; and (ii) a dehydrogenation component comprising at least one metal selected from Group 10 of the Periodic Table of Elements;
   (b) terminating contact of the dehydrogenation catalyst with additional cyclohexanone; then
   (c) contacting the dehydrogenation catalyst with hydrogen gas at a temperature of at least 300° C., a pressure of about 100 to about 3550 kPa, a weight hourly space velocity of about 0.2 to 50 $hr^{-1}$, and a hydrogen to cyclohexanone molar ratio of about 2 to about 20; and then
   (d) recontacting the dehydrogenation catalyst with additional cyclohexanone.

17. A process for the dehydrogenation of cyclohexanone to produce phenol, the process consisting of:
   (a) contacting cyclohexanone in a reaction zone under dehydrogenation conditions with a dehydrogenation catalyst comprising (i) a support comprising silica; and (ii) a dehydrogenation component comprising at least one metal selected from Group 10 of the Periodic Table of Elements;
   (b) terminating contact of the dehydrogenation catalyst with additional cyclohexanone; then
   (c) contacting the dehydrogenation catalyst with hydrogen gas at a temperature of at least 300° C., a pressure of about 100 to about 3550 kPa, a weight hourly space velocity of about 0.2 to 50 $hr^{-1}$, and a hydrogen to cyclohexanone molar ratio of about 2 to about 20; and then
   (d) recontacting the dehydrogenation catalyst with additional cyclohexanone.

\* \* \* \* \*